(12) United States Patent
Neumann

(10) Patent No.: US 6,570,011 B1
(45) Date of Patent: May 27, 2003

(54) METHOD FOR PRODUCING A STABILIZED AQUEOUS ALKALI METAL-2-HYDROXY-4,6-DICHLORO-S-TRIAZINE SOLUTION AND THE USE THEREOF

(75) Inventor: Thomas Neumann, Trostberg (DE)

(73) Assignee: Degussa AG, Trostberg (DE)

( * ) Notice: Subject to any disclaimer, the term of this patent is extended or adjusted under 35 U.S.C. 154(b) by 0 days.

(21) Appl. No.: 09/786,734

(22) PCT Filed: Sep. 9, 1999

(86) PCT No.: PCT/EP99/06671

§ 371 (c)(1),
(2), (4) Date: Mar. 8, 2001

(87) PCT Pub. No.: WO00/15619

PCT Pub. Date: Mar. 23, 2000

(30) Foreign Application Priority Data

Sep. 10, 1998 (DE) .......................................... 198 41 383

(51) Int. Cl.$^7$ ............................................. C07D 251/70
(52) U.S. Cl. ....................................... 544/217; 544/218
(58) Field of Search .................................. 544/217, 218

(56) References Cited

U.S. PATENT DOCUMENTS 3,325,287 A * 6/1967 Yamamoto et al. ........... 96/111
4,181,529 A * 1/1980 Sels et al. ...................... 96/111

FOREIGN PATENT DOCUMENTS

| CS | 223 478 B | | 10/1983 |
|---|---|---|---|
| DE | 28 20 108 A | | 11/1978 |
| DE | 29 10 726 A | | 10/1979 |
| EP | 0 616 071 | * | 12/1994 |
| JP | 59 106474 A | | 6/1984 |
| SU | 1 051 082 | | 10/1983 |

OTHER PUBLICATIONS

Chem. Abstracts. vol. 102, No. 2, Jan. 28, 1985, J. Arient Aqueous Solution of . . . triazine.

Chem. Abstracts. vol. 102, No. 2, Jan. 14, 1985—Preparation of . . . Hardening Agent.

Chem. Abstracts. vol. 100, No. 12, Mar. 19, 1984; Shakirov "Hardener based on monosodium . . . triazine".

* cited by examiner

*Primary Examiner*—John M. Ford
*Assistant Examiner*—Venkataraman Balasubrasubramanian
(74) *Attorney, Agent, or Firm*—Fulbright & Jaworski L.L.P.

(57) ABSTRACT

This invention relates to a process for the preparation of a stabilized aqueous alkali metal-2-hydroxy-4,6-dichloro-s-triazine (AHDT) solution, which entails starting at 5 to 40° C. with a solution containing either the corresponding alkali hydrogencarbonate, acetone, or a mixture thereof, and then, while cooling, adding cyanuric chloride and an alkali lye simultaneously in such a manner that the reaction temperature does not exceed 25° C. and the pH does not drop below 5.5, and during a subsequent stirring time of 2 to 30 hours adding either a very small quantity of alkali lauryl sulfate if the original starting solution contained hydrogencarbonate, or adding alkali hydrogencarbonate if exclusively acetone was used in the first reaction step, and then finally adding an alkali borate and/or a dialkali hydrogenphosphate and/or potassium hexacyanoferrate (II) as buffer. The pH, which should be $\geq 7.0$ during the entire process, may, if necessary, be adjusted with an acid to a value between 8.0 and 9.5. The invention also provides for the same alkali metal to be used in all steps of the process. In particular as a result of the alkali hydrogencarbonate co-stabilizer, one obtains with this relatively simple process, after very short reaction times, AHDT solutions which remain stable for a long time and which do not release $CO_2$ at any time during their synthesis, storage or use.

15 Claims, No Drawings

METHOD FOR PRODUCING A STABILIZED AQUEOUS ALKALI METAL-2-HYDROXY-4,6-DICHLORO-S-TRIAZINE SOLUTION AND THE USE THEREOF

This invention relates to a process for the preparation of a stabilized aqueous alkali metal-2-hydroxy-4,6-dichloro-s-triazine (AHDT) solution and use thereof.

The alkali metal and alkaline earth metal salts of 2-hydroxy-4,6-dichloro-s-triazine, especially the sodium salt thereof (NHDT), are preferred hardening agents for gelatinous materials which are used in particular for photographic purposes. Accordingly, there are numerous known methods of preparing these triazine derivatives, and also of hardening solutions containing them.

However, the stability of the hardening solutions remains problematic. This is because both during synthesis and storage of the carbonate-containing hardening solutions, and often during their use, carbon dioxide is formed and the triazines are hydrolyzed to the corresponding monochlorinated compounds. Another particular disadvantage connected with the formation of carbon dioxide is that the gas generates bubbles in the photographic layers produced with the hardening agent.

To overcome these difficulties, it has been suggested in the past that the aqueous hardening solutions be buffered with a water-soluble borate (DE-OS 28 20 108). According to the DE-OS 29 10 726, the buffering effect can be enhanced by means of an alkali metal hydroxide and possibly by addition of water-soluble organic solvents, for example acetone, which are inert under the reaction conditions. The amount of alkali borate used in this case is only 0.02 to 2 moles per mole AHDT.

It has been found in practice, however, that neither the sole measure of buffering with borates nor the additional use of alkali metal hydroxides solves the problem of carbon dioxide formation. A further disadvantage of the known synthesis method is the very slow formation of the respective alkali metal-2-hydroxy-4,6-dichloro-s-triazine (AHDT).

The object of this invention was thus to provide a process for the preparation of a stabilized aqueous alkali metal-2-hydroxy-4,6-dichloro-s-triazine (AHDT) with which, in particular, undesirable formation of $CO_2$ is suppressed both during the synthesis reaction and during storage and use of the prepared AHDT solution. In addition, the preparation process should be easy and quick to carry out.

This object was established by (a) providing an aqueous alkali hydrogencarbonate and/or acetone starting solution, (b) adding cyanuric chloride and an alkali lye under such conditions that the temperature does not rise above 25° C. and the pH does not drop below 5.5;

(c) adding an alkali salt of an organic acid for the case that in (a) a hydrogencarbonate-containing solution was used, or adding an alkali hydrogen carbonate for the case that in (a) exclusively acetone was used;

(d) adding a stabilizer selected from an alkali borate and/or an alkali (hydrogen) phosphate and/or an alkali hexacyanoferrate (II), and (e) if necessary adjusting the pH to the desired value with acid.

In a preferred embodiment, the process is conducted at temperatures between 5 and 40° C. in the following way:

(a) providing an aqueous 0.1 to 1.0 wt. % alkali hydrogencarbonate solution and/or a 0.5 to 5 wt. % acetone solution as starting solution, followed by (b) adding 8 to 16 wt. % cyanuric chloride, expressed in terms of the solution from (a); wherein during the addition of cyanuric chloride, 1 equivalent expressed in terms of cyanuric chloride of a 25 to 50 wt. % alkali lye, is added at a temperature not exceeding 25° C. to the suspension in such a manner that the pH of the reaction mixture does not drop below 5.5;

(c) subsequently adding, during a stirring period of 2 to 30 hours, 0.1 to 1.5 wt. ‰ of an alkali lauryl sulfate for the case that in (a) a hydrogen-carbonate-containing solution was used, or of 0.5 to 1.0 wt. % of alkali hydrogen carbonate for the case that in a) exclusively acetone was used, both weight precentages being expressed in terms of the overall solution;

(d) finally, adding 0.3 to 1.2 wt. %—expressed in terms of the overall solution—of an alkali borate and/or of dialkali hydrogenphosphate and/or of potassium hexacyanoferrate (II), and (e) if necessary, adjusting the pH to a value in the range from 8 to 9.5 with an acid.

Surprisingly, it was found that very small amounts of acetone or even the complete absence of acetone have no deleterious effect at all on the course of the reaction or on the reaction time. In view of the known prejudice—contained, for example, in the DE-OS 29 10 726—this was in no way to be expected. Moreover, particularly the use of alkali hydrogen carbonate permits wide variation in the way the process is conducted, it being possible at any time to quantitatively buffer the theoretically forming carbon dioxide.

Due to the use of alkali hydrogen carbonate, the process according to the invention indeed permits a wider temperature range, for example from 5 to 40° C., although temperatures between 10 and 20° C. are preferred. However, these relatively low temperatures have no deleterious effect whatsoever on the speed of reaction of the overall process.

For the process described here, sodium and potassium are preferred as alkali metals and have proved highly suitable. Using the same alkali metal for all steps of the process has the advantage that one obtains the pure sodium- or pure potassium-2-hydroxy-4,6-dichloro-s-triazine; however, it is also possible to use mixtures of these products.

The respective alkali hydrogencarbonate can be provided as aqueous starting solution, in which case a 0.5 to 0.8 wt. % solution is preferred. Alternatively, it can be added later on in the process, namely in step (c), if in step (a) aqueous acetone solution was used exclusively—according to the invention preferably in an amount of 1.0 to 2.0 wt. %. It is also possible, however, to start with a mixture consisting of alkali hydrogencarbonate and acetone in arbitrary proportions, provided amounts are within the range claimed.

The choice of alkali lye for step (b) will depend on which alkali hydrogencarbonate is used: if $NaHCO_3$ is used in step a) and/or step (d), it is preferable to add NaOH, whereas if $KHCO_3$ is used, it is preferable to add potassium lye in step (b).

All in all, there are thus no strict parameters governing the way in which the process of the invention is conducted. To optimize the course of the reaction, however, it is recommended that the amount of cyanuric chloride used in step (b) preferably be in the range from 10 to 12 wt. % expressed in terms of the solution from (a). The reaction sequence is likewise speeded up by selecting a preferred stirring time of 3 to 6 hours in step (c).

Like the alkali lye in step (b), the alkali salt added in step (c)—preferably the alkali salt of a $C_{10}$–$C_{20}$ organosulfuric acid, in particular alkali lauryl sulfate—can be selected specifically to match the respective alkali hydrogencarbonate and thus to ensure a pure product.

As already explained, the principal objective of developing the process claimed here was to suppress the undesirable formation of $CO_2$. This objective is achieved among other things by the addition of stabilizing and buffering substances in step (d) of the process according to the invention, preference being given to the alkali borates $Na_2B_4O_7$ or $K_2B_4O_7$, their respective pentahydrates or decahydrates or mixtures thereof; as representatives of the alkali (hydrogen) phosphates, which are likewise suitable according to the invention, trialkali phosphates, alkali hydrogenphosphates and, in particular, dialkali hydrogenphosphates such as disodium and dipotassium hydrogenphosphate are preferred; the choice may again depend on the alkali hydrogencarbonate selected in each case.

For the most part, the pH does not constitute a limiting parameter for the process claimed. However, to ensure complete hydrolysis of the cyanuric chloride, it may be necessary according to the invention to adjust the pH at the end of step (d) to a value between 8.0 and 9.5 using an acid; wherein a mineral acid is recommended, preferably hydrochloric acid. It is especially beneficial if the pH is in the range from 8.5 and 9.0 for step (e). It is altogether beneficial for the course of the reaction according to the invention if the pH of the reaction mixture in steps (a) to (d) is $\geq 7.0$.

In cases where step (c) requires addition of organic alkali salt, spent $NaHCO_3$ or $KHCO_3$ can be replaced by adding it at the same time; an excess of alkali hydrogencarbonate has been found to have no deleterious effect whatsoever on the stability of the AHDT solution because any $CO_2$ which may have formed dissolves completely in the nascent sodium- or potassium-2-hydroxy-4,6-dichloro-s-triazine solutions.

Certain requirements for the AHDT solutions prepared according to the process claimed may likewise necessitate that the stabilized solution be additionally clarified. To this end, the invention provides for filtration of the solutions following step (d) or (e). Filtration can be preceded by the addition of activated carbon.

The stabilized aqueous solutions of sodium- or potassium-2-hydroxy-4,6-dichloro-s-triazine are used preferably for hardening gelatin or for textile or paper finishing.

All in all, this invention provides a process which permits unproblematic preparation of stabilized aqueous AHDT solutions. The use of alkali hydrogencarbonates as co-stabilizers has proved insofar beneficial as the entire duration of the process is reduced drastically as a result. It is also possible, if desirable, to dispense entirely with acetone.

Stabilized aqueous alkali metal-2-hydroxy-4,6-dichloro-s-triazine solutions containing less than 4.0 wt. %, preferably less than 2.5 wt. % acetone, are also subject matter of the invention. Solutions which contain no acetone or other organic solvents are especially preferable. It is beneficial if the solutions have a pH$\geq$7.0, and especially beneficial if the pH is in the range from 8.0 to 9.5. In addition, the solutions preferably show a pH stability (pH$\geq$7.0 during storage at room temperatur (e) of at least 100 days or, especially preferable, of at least 250 days.

The following examples illustrate the advantages of the invention.

EXAMPLES

Example 1

4500 kg of an aqueous 0.5 wt. % solution of $NaHCO_3$ were introduced into a stirred-tank reactor at 20° C. The pH was >8.5. The calculated amount of cyanuric chloride (450 kg=9 wt. % expressed in terms of the aqueous hydrogencarbonate solution) was then added. While the cyanuric chloride was being added, metered addition of a 25% NaOH solution (783 kg) was begun with strong cooling. The pH was >8. During a post-reaction period, 0.013 wt. % of sodium lauryl sulfate (0.75 kg) was added; spent $NaHCO_3$ was replaced. The solution was stabilized by addition of 0.5 wt. % sodium tetraborate (28.6 kg), and the pH adjusted to 8.5 by addition of hydrochloric acid. The solution obtained in this way was then filtered in order to remove particulate matter and clarify it.

Storage Tests at Room Temperature

| Days | 0 (start) | 47  | 69  | 99  | 116 | 256 |
|------|-----------|-----|-----|-----|-----|-----|
| pH   | 8.5       | 7.8 | 7.7 | 7.6 | 8.0 | 8.0 |

By comparison, a solution with no added stabilizer turns acidic (pH=1) after just 8 weeks' storage at room temperature.

Example 2

4500 kg of an aqueous 0.5 wt. % solution of $NaHCO_3$ were introduced into a stirred-tank reactor at 20° C. The pH was >8.5. The calculated amount of cyanuric chloride (450 kg=9 wt. % expressed in terms of the aqueous hydrogencarbonate solution) was then added. While the cyanuric chloride was being added, metered addition of a 25% NaOh solution (783 kg) was begun with strong cooling. The pH was >8. During a post-reaction period, 0.013 wt. % of sodium lauryl sulfate (0.75 kg) was added; spent $NaHCO_3$ was replaced. The solution was stabilized by addition of 0.5 wt. % disodium hydrogenphosphate (28.6 kg), and the pH adjusted to 8.5 by addition of hydrochloric acid. The solution obtained in this way was then filtered in order to remove particulate matter and clarify it.

Storage Tests at Room Temperature

| Days | 0 (start) | 47  | 69  | 116 | 156 |
|------|-----------|-----|-----|-----|-----|
| pH   | 8.5       | 7.0 | 7.6 | 8.0 | 8.0 |

By comparison, a solution with no added stabilizer turns acidic (pH=1) after just 8 weeks' storage at room temperature.

Example 3

1.75 l deionized water with 2 wt. %—expressed in terms of the overall solution—of acetone were introduced at 18° C. into a four-necked flask equipped with a stirrer, pH electrode, thermometer, automatic metering unit and powder funnel. Subsequently, 9.4 wt. %—expressed in terms of the aqueous acetone solution—of cyanuric chloride (177g) were added quickly. At a controlled pH, 307.2 g of a 25% NaOH solution were added to the suspension, starting from the time of addition of cyanuric acid. The reaction temperature was kept below 25° C. After about 6 hours, 62% of the calculated amount of NaOH had been added. The clear solution, having been subsequently stirred at room temperature for 24 hours at a controlled pH (pH=8.5), was then adjusted to pH 9.0 (99.9% of the calculated amount of NaOH have been used up). 14.6 g $NaHCO_3$ (0.65 wt. %) were added, whereupon the pH sank to 8.1. It was adjusted to 8.5 by addition of 11.2 g sodium tetraborate (0.5 wt. %) and hydrochloric acid. The reaction solution was stirred for 2 hours with 2 g of activated carbon. To remove the activated carbon, the solution was filtered with a nutsch filter. A stable solution was obtained.

Storage Tests at Room Temperature

| Days | 0 (start) | 12 | 28 | 43 | 63 | 195 | 256 |
|---|---|---|---|---|---|---|---|
| pH | 8.5 | 8.3 | 8.2 | 8.5 | 8.8 | 8.1 | 8.0 |

By comparison, a solution with no added stabilizer turns acidic (pH=1) after just 8 weeks' storage at room temperature.

Example 4

1.75 l deionized water with 2 wt. %—expressed in terms of the overall solution—of acetone were introduced at 18° C. into a four-necked flask equipped with a stirrer, pH electrode, thermometer, automatic metering unit and powder funnel. Subsequently, 9.4 wt. %—expressed in terms of the aqueous acetone solution—of cyanuric chloride (177 g) were added quickly. At a controlled pH, 307.2 g of a 25% NaOH solution were added to the suspension, starting from the time of addition of cyanuric acid. The reaction temperature was kept below 25° C. After about 6 hours, 62% of the calculated amount of NaOH had been added. The clear solution, having been subsequently stirred at room temperature for 24 hours at a controlled pH (pH=8.5), was then adjusted to pH 9.0 (99.9% of the calculated amount of NaOH have been used up). 14.6 g $NaHCO_3$ (0.65 wt. %) were added, whereupon the pH sank to 8.1. It was raised to 8.5 by addition of caustic lye of soda. The solution was stabilized by addition of 2.3 g potassium hexacyanoferrate (II) (0.1 wt. %).

Storage Tests at Room Temperature

| Days | 0 (start) | 12 | 28 | 43 | 63 | 195 | 256 |
|---|---|---|---|---|---|---|---|
| pH | 8.5 | 8.3 | 7.5 | 7.8 | 8.2 | 8.0 | 8.0 |

By comparison, a solution with no added stabilizer turns acidic (pH=1) after just 8 weeks' storage at room temperature.

What is claimed is:

1. A process for the preparation of a stabilized aqueous alkali metal-2-hydroxy-4,6-dichloro-s-triazine solution, wherein
   (a) providing at least one of an aqueous alkali hydrogencarbonate or an aqucous acetone solution as a starting solution;
   (b) adding cyanuric chloride and an alkali lye to said starting solution under such conditions that the temperature does not rise above 25° C. and the pH does not drop below 5.5;
   (c) adding an alkali salt of $C_{10}$–$C_{20}$ alkyl sulfate if in step (a) said starting solution is an alkali hydrogencarbonate containing solution, or adding an alkali hydrogencarbonate if in step (a) said starting solution is an exclusively aqueous acetone solution;
   (d) adding at least one stabilizer selected from the group consisting of an alkali borate, an alkali (hydrogen) phosphate and an alkali hexacyanoferrate (II); and
   (e) if necessary, adjusting the pH to the desired value with an acid.

2. The process of claim 1,
   wherein at temperatures between 5 and 40° C.
   in step (a) an aqueous 0.1 to 1.0 wt. % alkali hydrogencarbonate solution and/or a 0.5 to 5 wt. % acetone solution is provided as starting solution, to which thereafter in step (b) 8 to 16 wt. % cyanuric chloride, expressed in terms of the solution from (a), is added, wherein 1 equivalent expressed in terms of cyanuric chloride of a 25–50. wt. % alkali lye is added during the addition of cyanuric chloride at a temperature not exceeding 25° C. to the suspension in such a manner that the pH of the reaction mixture does not drop below 5.5, and in step (c) thereafter, during a stirring period of 2 to 30 hours, 0.1 to 1.5 wt. % of an alkali lauryl sulfate is added for the case that in step (a) a hydrogencarbonate-containing solution was used, or 0.5 to 1.0 wt. % of alkali hydrogencarbonate is added for the case that in step (a) exclusively aqueous acetone solution was used, both weight percentages being expressed in terms of the overall solution, and in step (d) 0.3 to 1.2 wt. %, expressed in terms of the overall solution, of an alkali borate and/or of a dialkali hydrogenphosphate and/or of potassium hexacyanoferrate (II) is added, and in step (e) the pH is adjusted if necessary to a value in the range from 8 to 9.5.

3. The process of claim 1, wherein the temperature is between 10 and 20° C.

4. The process according to claim 1, wherein sodium or potassium ions are used as alkali metal ions.

5. The process according to claim 1, wherein the same alkali metal ion is used in all steps of the process.

6. The process according to claim 1, wherein an aqueous 0.5 to 0.8% alkali hydrogencarbonate solution and/or an aqueous 1.0 to 2.0% acetone solution is used as starting solution in step (a) of the reaction.

7. The process according to claim 1, wherein 10 to 12 wt. % of cyanuric chloride, expressed in terms of the solution from (a), is added in reaction step (b).

8. The process according to claim 1 wherein the stirring time in step (c) of the reaction is 3 to 6 hours.

9. The process according to claim 1, wherein $Na_2B_4O_7$, $K_2B_4O_7$, their respective pentahydrate or decahydrates or mixtures thereof are used as alkali borate.

10. The process according to claim 1, wherein the reaction mixture in reaction steps (a) to (d) has a pH≧7.0.

11. The process according to claim 1, wherein in step (e) said acid is a mineral acid.

12. The process of claim 11, wherein said mineral acid is hydrochloric acid.

13. The process according to claim 1, wherein the pH is adjusted in reaction step (e) to a value in the range from 8.5 to 9.0.

14. The process according to claim 1, wherein the stabilized solution is filtered following reaction step (d) or (e), optionally through addition of activated carbon.

15. The process according to claim 1, wherein in reaction step (c), if an alkali salt of a $C_{10}$–$C_{20}$ alkyl sulfate is added, spent alkali hydrogencarbonate is replaced.

* * * * *